United States Patent [19]

Kubota

[11] Patent Number: 4,538,610
[45] Date of Patent: Sep. 3, 1985

[54] RESECTOSCOPE

[75] Inventor: Tetsumaru Kubota, Hachioji, Japan

[73] Assignee: Olympus Optical Co., Ltd., Tokyo, Japan

[21] Appl. No.: 454,653

[22] Filed: Dec. 30, 1982

[30] Foreign Application Priority Data

Jan. 14, 1982 [JP] Japan ............................. 57-3506[U]

[51] Int. Cl.³ .............................................. A61B 17/39
[52] U.S. Cl. ............................................... 128/303.15
[58] Field of Search ....................................... 128/4–8,
128/303.13, 303.15, 783–786, 303.14, 303.17;
403/195, 221–222

[56] References Cited

U.S. PATENT DOCUMENTS 2,487,502 11/1949 Willinsky ..................... 128/303.15
4,149,538 4/1979 Mrava et al. ................. 128/303.15

Primary Examiner—Lee S. Cohen
Assistant Examiner—Steven Falk
Attorney, Agent, or Firm—Armstrong, Nikaido, Marmelstein & Kubovcik

[57] ABSTRACT

A resectoscope comprising a resecting sheath, an observing scope positioned in the sheath and an electrode having a forward and rear end positioned in the sheath. An electrode fixing member comprising an electrically conductive flexible fixing portion is provided which has a slit therein for receiving the rear end of the electrode. Electrically insulating pressing means press the flexible fixing portion into engagement with the electrode and an electrical plug receiving member with an opening therein is electrically connected to the fixing portion for receiving an electrical plug in the opening and connecting the plug to the electrode through the fixing portion. An electrically insulating moving member surrounds the fixing portion, the movable member being movable with respect to the sheath such that the movement of the movable member moves the fixing portion and the electrode fixed therein whereby the front portion of the electrode is extended out of the sheath.

6 Claims, 6 Drawing Figures

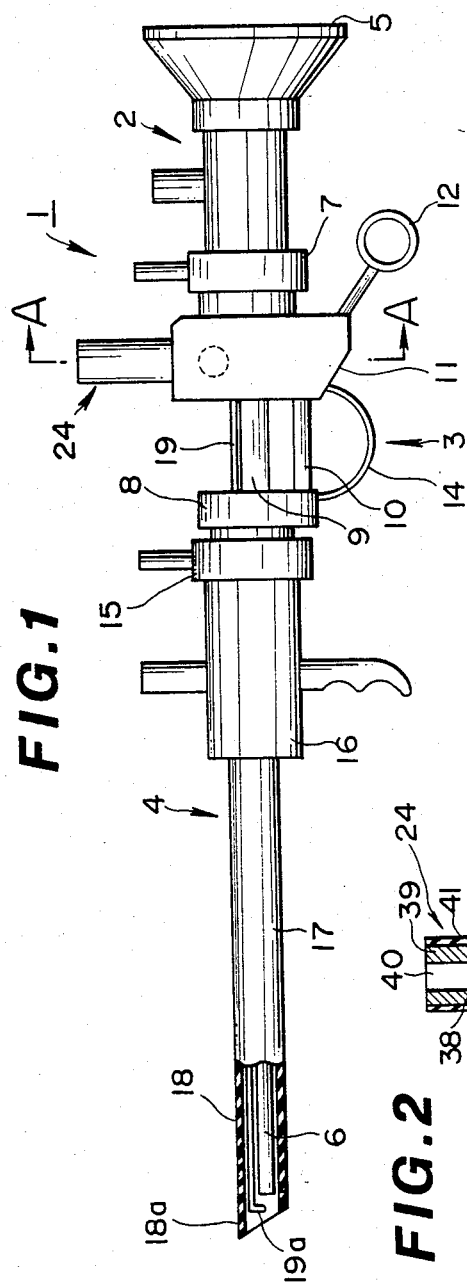
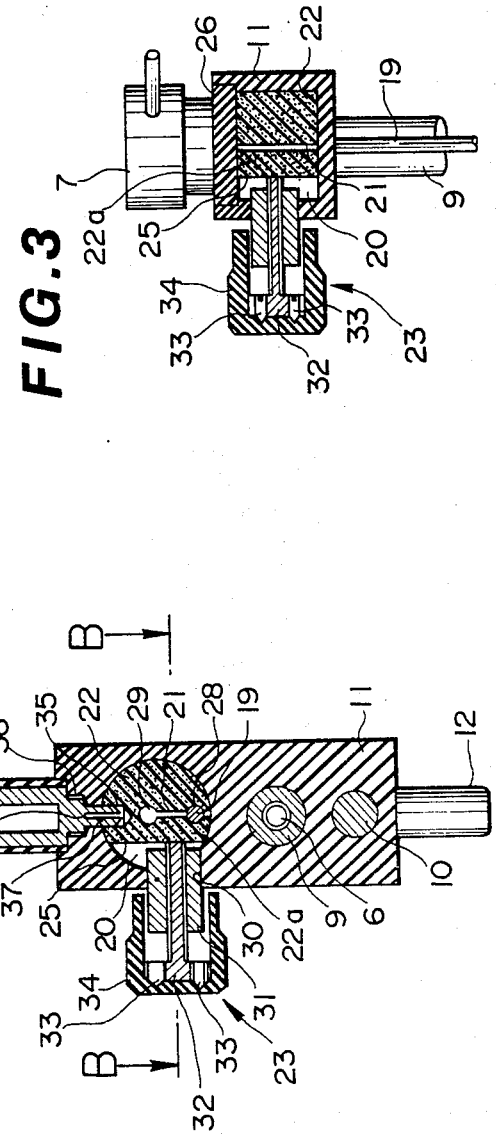
FIG. 1
FIG. 2
FIG. 3

RESECTOSCOPE

BACKGROUND OF THE INVENTION

This invention relates to a resectoscope which is inserted into a bladder through the urethra and has an electrode projected on the tip side through which a high frequency electric current can be passed while an affected part is being sighted so that the affected part may be resected.

The above mentioned resectoscope comprises a scope (optical sighting tube), an electrode, a resectoscope sheath through which the scope and electrode are inserted, a grip provided to project below the rear part of this resectoscope sheath and a movable member fixing the above mentioned electrode at the rear end and provided with a finger hanger so that, when fingers of one hand are inserted in the grip of the above mentioned resectoscope sheath and the finger hanger of the movable member to grip them so as to slide and reciprocate the movable member forward and rearward, that is, by making the fingers approach each other and separate from each other, the electrode on the tip side will be advanced and retreated from an opening at the tip of the resectoscope sheath to make a resection or the like.

However, in the conventional resectoscope, the resecting electrode is electrically connected at the rear end with the electrode cord by the following formation.

That is to say, while an electrode inserting hole is made from the tip surface of the above mentioned movable member to the rear middle, on the respective side surfaces of the movable member in the positions holding this inserting hole, a mouthpiece inserting hole having a plug inserting hole in which the plug at the tip of the electrode cord is inserted and a separate pressing member inserting hole are opened so as to face the above mentioned electrode inserting hole. The electrode inserted in this electrode inserting hole is pressed at the rear end on a mouthpiece inserted through the above mentioned mouthpiece inserting hole in the opposite position on the tip surface of a pressing member formed to be comparatively small and inserted through the pressing member inserting hole so that the electrode may be pressed at the rear end on the mouthpiece. The high frequency current fed from the current source may be passed to the electrode through the electrode cord, the plug at the tip of the electrode cord and the mouthpiece having the inserting hole in which this plug is inserted.

In such conventional structure of connecting the electrode with the mouthpiece, the electrode is pressed at the rear end into contact with the mouthpiece with the pressing force at the tip of a small diameter pressing member. Therefore, there have been problems that, in order that the electrode may be well connected with the mouthpiece, not only the pressing member and the mouthpiece with the electrode held between them must be aligned with each other in the producing process so as to be correctly opposed to each other but also, unless they are aligned with each other with high precision, the electric contact of the electrode with the mouthpiece will fail.

Also, in this case, when the pressing force applied to the pressing member is very large or under repeated use with the lapse of time in which the pressing force applied to the pressing member is repeatedly alternately released and given, the surface of contact of the pressing member at the tip with the electrode at the rear end or the surface of contact of the electrode at the rear end with the mouthpiece will be worn or damaged. As a result, there have been problems that the electric contact will fail on the surface of contact of the electrode at the rear end with the mouthpiece, therefore no high frequency current will be fed to the electrode and the affected part will not be able to be well resected.

Further, there is suggested in U.S. Pat. No. 2,487,502 a prior art wherein the electrode and electrode cord are electrically connected with each other as described below.

In this prior art, a mouthpiece to which the electrode cord is connected is formed to be plate-shaped at the tip and a slit is provided at the tip so as to hold the electrode at the rear end in this slit. A tightening screw is arranged in the direction at right angles with the slit so as to pull a holding piece on the side beyond the slit toward the hand side, to hold the electrode at the rear end within the slit and to electrically connect the electrode to the above mentioned mouthpiece.

However, in such prior art, there have been problems that, as a telescope can be further insulatively inserted through the above mentioned mouthpiece, the telescope and electrode can be rotatably fitted and the telescope is arranged in the center, the tightening screw will be arranged toward one side end of the body, the fitting structure for fitting this tightening screw to the body will be complicated and the production cost will be high.

Further, there has been a danger that, as the above mentioned mouthpiece part is exposed, the operator will accidentally touch the mouthpiece part so as to be electrified.

There have been further problems that the moisture and dust will be deposited on the outer surface so that the insulation will not be sufficient, even if the device is insulated from direct currents, the high frequency dielectric loss will be so large that the insulation will be insufficient, when the capacity is formed, the high frequency insulation will become insufficient and, in case the current is passed, there will be a danger of being electrified and the safety will be low.

BRIEF SUMMARY OF THE INVENTION

An object of the present invention is to provide a resectoscope wherein an electrode at the rear end can be electrically connected with an electrode cord at the tip without failing the contact.

Another object of the present invention is to provide a resectoscope wherein an electrode at the rear end can be electrically connected with an electrode cord at the tip with a simple structure.

A further object of the present invention is to provide a resectoscope having no danger of being electrified and high in the safety.

Another object of the present invention is to provide a resectoscope wherein an electrode can be connected and fixed at the rear end without being collapsed or broken to be damaged.

Other objects, features and advantages of the present invention will become apparent enough with the following explanation.

BRIEF DESCRIPTION OF THE DRAWINGS

FIGS. 1 to 3 relate to a first embodiment of the present invention.

FIG. 1 is a side view of the first embodiment.

FIG. 2 is a sectioned view on line A—A in FIG. 1.

FIG. 3 is a sectioned view on line B—B in FIG. 2.

FIG. 4 is a sectioned view of the second embodiment.

FIG. 5 is a sectioned view on line C—C in FIG. 4.

FIG. 6 is a sectioned view of the third embodiment.

DETAILED DESCRIPTION OF THE INVENTION

Figure 4:
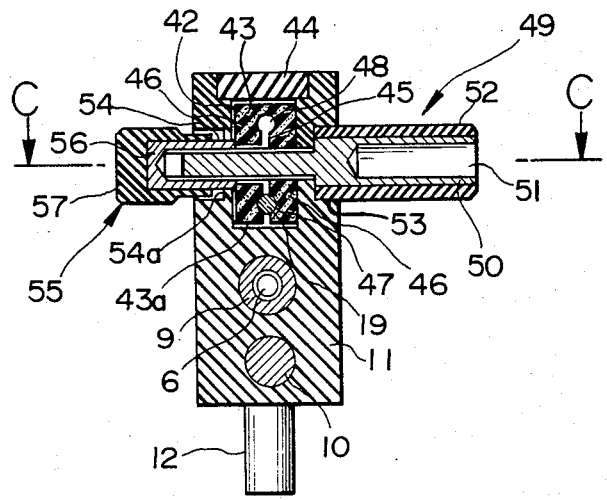
FIGS. 4 and 5 relate to a second embodiment of the present invention.

In FIGS. 1 to 3, a resectoscope 1 of the first embodiment of the present invention is formed of a scope 2, a resectoscope handle 3 to which this scope 2 is removably fitted and a resectoscope sheath 4 removably fitted to this resectoscope handle 3. The scope 2 comprises an eyepiece part 5 and a scope inserting part 6. This scope 2 and resectoscope handle 3 are removably connected with each other through a connecting part 7 provided in the resectoscope handle 3. The resectoscope handle 3 connects the above mentioned connecting part 7 and a forward fixed member 8 with each other through a guide pipe 9 and guide shaft 10. A movable member 11 is slidably fitted to the guide pipe 9 and guide shaft 10. A finger hanger 12 is fitted to this movable member 11. This movable member 11 and fixed member 8 are connected with each other, for example, through a plate spring 14. Also, the resectoscope handle 3 and resectoscope sheath 4 are removably connected with each other through a connecting part 15 provided on the resectoscope sheath 4. The resectoscope sheath 4 comprises the connecting part 15 with the resectoscope handle 3, a resectoscope sheath body 16 and a resectoscope sheath inserting part 17. The resectoscope sheath inserting part 17 is formed of an outer tube 18 formed of metal such as brass or stainless steel and an insulated tip part 18a formed of such insulating member as an epoxy resin or ceramics and fitted to the tip of the outer tube 18. The scope inserting part 6 is inserted through the guide pipe 9 of the resectoscope handle 3 in an internal path of this outer tube 18. An electrode 19 is inserted as provided parallelly with this scope inserting part 6. This electrode 19 has, for example, a loop-shaped electrode tip 19a provided to project at the tip so as to be able to resect an affected part (prostate) as heated by passing an electric current.

This electrode 19 is borne and held at the rear end by an electrode fixing structure shown in FIG. 2 and is to be electrically connected to an external electrode cord for feeding an electric current to this electrode 19.

This electrode fixing structure is formed of a resilient electrode fixing member 22 arranged within a space 20 formed by partly boring the interior of the movable member 11 formed of such highly insulative material as Teflon to hold the electrode 19 at the rear end with a flexible piece 22a formed by providing a slit 21, a pressing part 23 pressing a pressed surface 25 of the flexible piece 22a to narrow the width of the above mentioned slit 21 and an electrode cord connecting part 24 electrically connected at the tip to the above mentioned electrode fixing member 22.

The space 20 formed by boring the above mentioned movable member 11 is in the form of a column having an opening for inserting the electrode fixing member 22 on the rear end surface of this movable member 11 as shown in FIG. 3 and is so formed that its axial direction may be parallel with the above mentioned electrode 19.

The electrode fixing member 22 is formed of a conductive member to be in the form of a column of the same shape as of the above mentioned space 20 but slightly shorter than it, is closed in the rear with a lid 26 formed of such insulator as Teflon and shown in FIG. 3 and is arranged within the above mentioned space 20. The slit 21 is formed in this electrode fixing member 22. The rectangular pressed surface 25 is formed on the side surface of this electrode fixing member 22 by cutting off one side part of it. The flexible piece 22a is formed of a thin part between this pressed surface 25 and slit 21.

The above mentioned slit 21 opens on the lower side surface of the electrode fixing member 22 and is formed to be of a proper depth in the diametral direction of this electrode fixing member 22 and to be parallel with the above mentioned pressed surface 25 formed from the tip surface to the electrode fixing member 22. An electrode holding space 28 of a circular section having substantially the same diameter as the diameter of the rear end pat of the above mentioned electrode 19 is formed in a position near the outer periphery on which this slit 21 opens. In the deepest part of this slit 21, an expanded part 29 for giving a resiliency to the above mentioned flexible piece 22a is formed from the tip to the rear end of the slit 21 in the direction of the electrode 19 to be held.

The pressing part 23 pressing the above mentioned pressed surface 25 is fitted in an opening (through hole) 30 formed on the side surface of the movable member 11 so as to face the pressed surface 25 of the electrode fixing member 22. This pressing part 23 is formed of a guide tube 31 fitted and fixed in the opening 30 of the above mentioned movable member 11, inserted at the tip near to the above mentioned pressed surface 25 and having a female screw formed on the inside surface, a pressing rod 32 screwed with this guide tube 31 and advancing and retreating inward and outward as guided by the guide tube 31 so as to be able to contact the pressed surface 25 of the above mentioned flexible piece 22a and an insulative grip 34 fixed to the rear end part of this pressing rod 32 with screws 33. The movable member 11 and guide tube 31 may be integrally formed instead of separately as mentioned above. When the above mentioned grip 34 is rotated to be screwed, the pressing rod 32 will advance toward the above mentioned space 20 and will press at the tip the pressed surface 25 of the flexible piece 22a so as to narrow the width of the slit 21. When the pressing rod 32 is retreated, the width of the above mentioned slit 21 will be expanded by the resiliency of the flexible piece 22a.

The above mentioned electrode cord connecting part or receiving part 24 is formed of an engaging hole 35 of a proper depth formed on the side surface of the electrode fixing member 22, that is, on the upper side surface on the opposite side of the slit 21 on the lower side in the drawings (FIGS. 1 and 2) of this embodiment, a fitting opening 36 provided as steppedly expanded in the diameter toward the outside surface (upper outside surface) of the above mentioned movable member 11 to coaxially communicate with and expose this engaging hole 35, a connecting mouthpiece 39 inserted in this fitting opening 36 and pressed at the tip into the above mentioned engaging hole 35, a plug inserting hole 40 provided inward from the rear end surface (upper end surface) of this connecting mouthpiece 39 to insert the plug at the tip of the electrode cord and an insulating member r1 fitted around this connecting mouthpiece 39, pressed at the tip (lower end) into the above mentioned movable member 11 and made on the upper end surface flush with the upper end surface of the connecting mouthpiece 39.

The connecting mouthpiece 39 is formed in the tip part to be of a small diameter and has a slit 38 formed in this tip part so as to be able to be pressed into the engaging hole 35. Thus, the electrode fixing member 22 arranged within the movable member 11 is fixed to the movable member 11 by the connecting mouthpiece 39 engaged through the movable member 11 from the outside so as to be prevented from moving forward and rearward and rotating.

The thus formed first embodiment is characterized in that, in the resectoscope comprising the scope, electrode, resectoscope sheath in which the scope and electrode are inserted and movable member fixing the above mentioned electrode at the rear end, the electrode fixing member formed of the conductive material to fix the electrode at the rear end is internally provided within the movable member formed of the insulative material and is provided with the slit to form the flexible piece, the electrode holding space is formed within this slit and the pressing part pressing the flexible piece on the side surface to narrow the width of the electrode holding space and the plug connecting part to which the plug at the tip of the electrode cord is to be connected are fitted to the side surface of the above mentioned movable member.

Now, in the embodiment formed as described above, in order to bear the electrode 19 at the rear end with the above mentioned electrode fixing structure, first of all, the grip 34 of the pressing part 23 is loosened to release the pressing force applied to the flexible piece 22a of the electrode fixing member 22 and to expand the width of the slit 21 with the resiliency of the flexible piece 22a and then the electrode 19 is inserted at the rear end into the electrode holding space 28 formed in the slit 21 of the electrode fixing member 22. When the electrode 19 is inserted at the rear end for a predetermined length into the electrode holding space 28 and the grip 34 of the above mentioned pressing part 23 is rotated to be screwed, the pressing rod 32 will be advanced as guided by the guide tube 31 and the pressed surface 25 of the flexible piece 22a of the electrode fixing member 22 will be pressed by the tip surface of the pressing rod 32 to hold and fix the above mentioned electrode 19 at the rear end in the electrode holding space 28. At this time, as the electrode holding space 28 is formed to be of a cross-sectional shape substantially identical with that of the electrode 19, the electrode 19 will be held on the peripheral side surface of the rear end part uniformly and strongly by the electrode holding space 28. As soon as the electrode 19 is held by the electrode holding space 28, the electrode 19 will be electrically connected with the electrode cord so that a high frequency current may be fed to the electrode 19 on the tip side. Further, as the above mentioned connecting mouthpiece 39 is pressed into the engaging hole 35 of the electrode fixing member 22, this connecting mouthpiece 39 can prevent the forward and rearward movement and rotation of the electrode fixing member 22.

In such state, when the resectoscope 1 is held, fingers are hung on the finger hanger of the resectoscope sheath body 16 and the finger hanger 12 provided to project on the movable member 11 and a force is applied to make one finger hanger 12 approach the other finger hanger side, the movable member 11 will slide forward and the electrode 19 will project forward on the tip side out of the tip part 18a of the outer tube 18.

Therefore, when this projected electrode tip 19a is contacted with an affected part or the like, such part will be able to be resected.

After the resection, when the force applied to the above mentioned finger hanger 12 is weakened, due to the resiliency of the plate spring 14, the movable member 11 on which the finger hanger 12 is provided will slide rearward and the electrode tip 19a will also retreat rearward to be contained inside the outer tube tip part 18a.

Figure 5:
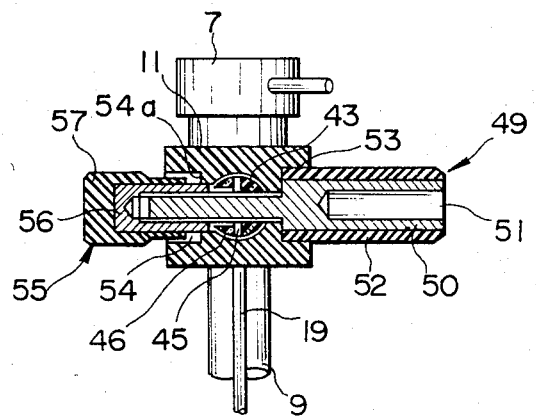

In the second embodiment shown in FIGS. 4 and 5, a space 42 formed in the movable member 11 is made cylindrical so that its axial direction may be at right angles with the arranging direction of the electrode 19. An opening for inserting an electrode fixing member 43 is formed at the upper end of this space 42.

The electrode fixing member 43 arranged within the above mentioned space 42 is formed of a conductive member to be of a shape substantially identical with that of this space 42 and to be slightly shorter in the axial direction and is arranged within the space 42 closed above with a lid 44 formed of an insulative member.

A slit 45 formed in this electrode fixing member 43 is opened to coincide with the arranging direction of the above mentioned electrode 19 on the circular bottom surface 43a of this electrode fixing member 43 and to pass through the diameter of the circle. This slit 45 is formed to be of a proper depth in the axial direction of the electrode fixing member 43 to form a flexible piece 46. Near the outer periphery on which this slit 45 opens, an electrode holding space 47 of a circular cross-section having a diameter substantially identical with that of the rear end of the electrode 19 is formed from the front end to the rear end of the slit 45. Further, in the deepest part of this slit 45, an expanded part 48 of a substantially circular cross-section is formed form the front end to the rear of the slit 45 so as to give a resiliency to the flexible piece 46.

The electrode cord connecting part 49 is formed of a connecting mouthpiece 50, a plug inserting hole 51 opening on the rear end surface of this connecting mouthpiece 50 and provided coaxially from the rear end surface toward the forward inside to insert the plug at the tip of the electrode cord and an insulating member 52 pressed at one large diameter side end slightly into the above mentioned movable member 11 and formed at the other side end to be flush with the rear end surface of the above mentioned connecting mouthpiece 50. The above mentioned connecting mouthpiece 50 is inserted at the tip through a fitting opening 53 formed on the side surface of the above mentioned electrode fixing member 43 as electrically connected with it, is then projected at the tip slightly out of an opening 54 formed on the opposite side surface of the movable member 11 and has a male screw provided on the outer periphery of the tip part. The connecting mouthpiece 50 passes through the electrode fixing member 43 to prevent it from moving forward and rearward and rotating.

The pressing part 55 made to press the side surface of the flexible piece 46 of the electrode fixing member 43 to narrow the width of the above mentioned slit 45 is fitted in an opening 54 for projecting the above mentioned connecting mouthpiece at the tip.

This pressing part 55 is formed of a pressing tube 56 having a female screw provided in the axial direction to be screwed with the male screw at the tip of the above mentioned connecting mouthpiece 50 and a grip 57 secured to the rear end of this pressing tube 56 to fit it with an insulative member so that, when this grip 57 is rotated to be screwed, the pressing tube 56 as guided by the tip part of the connecting mouthpiece 50 of the electrode cord connecting part 49 will advance into the movable member 11 through the clearance between the side surface of the tip part of the connecting mouthpiece 50 of this electrode cord connecting part 49 and the inner periphery of the opening 54 and will press with the tip surface one side surface of the flexible piece 46 of the electrode fixing member 43 to narrow the width of the slit 45. Further, the above mentioned opening 54 has a projecting step inside and has the clearance between the outer periphery of the pressing tube 56 and the opening 54 formed to be narrow to prevent electricity leakage.

Now, in the second embodiment formed as described above, in order to bear the electrode 19 at the rear end with the above mentioned electrode fixing structure, first of all, the grip 57 of the pressing part 55 is loosened to release the pressing force applied to the electrode fixing member 43 and to expand the width of the slit 45 with the resiliency of the flexible piece 46 and then the electrode 19 is inserted at the rear end into the electrode holding space 47 formed in the electrode fixing member 43. When the electrode 19 is inserted at the rear end for a predetermined length into this electrode holding space 47 and the grip 57 of the above mentioned pressing part 55 is rotated to be screwed, the pressing tube 56 will be advanced as guided by the top part of the connecting mouthpiece 50 and one side surface of the flexible piece 46 of the electrode fixing member 43 will be pressed by the tip surface of the pressing tube 56 so as to hold and fix the above mentioned electrode 19 at the rear end with the electrode holding space 47. At this time, as the electrode holding space 47 is formed to be of a cross-sectional shape substantially identical with that of the electrode 19, the electrode 19 will be held on the peripheral side surface uniformly and strongly by the electrode holding space 47. As soon as the electrode 19 is held by the electrode holding space 47, the electrode 19 will be electrically connected with the electrode cord so that a high frequency current may be fed to the tip side of the electrode 19.

As the above mentioned connecting mouthpiece 50 passes through the middle of the electrode fixing member 43, this electrode fixing member 43 will be prevented by the above mentioned connecting mouthpiece 50 from moving forward and rearward and rotating. Therefore, the electrode fixing member 43 can be fixed without requiring any other fixing means.

Figure 6:
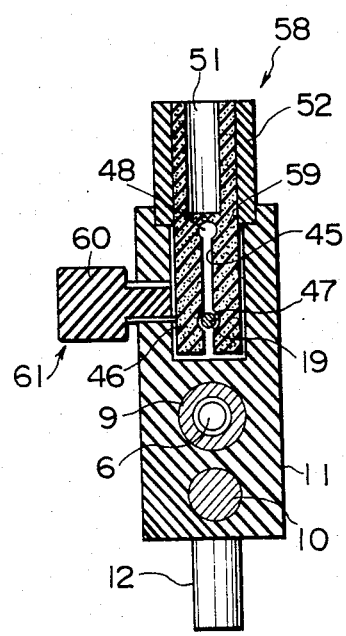
FIG. 6 relates to a third embodiment of the present invention.

In the third embodiment shown in FIG. 6, an electrode fixing member 59 is formed to be cylindrical so that its axis may be in the direction at right angles with the arranging direction of the electrode 19. An electrode cord connecting part 58 is integrally formed at one end of this electrode fixing member 59. A screw hole is formed in the movable member 11 on the outer periphery of the side part of the above mentioned electrode fixing member 59. An insulative pressing member 60 is screwed on the tip side into this screw hole is provided to project to form a pressing part 61 making it possible to press the flexible piece 46 having the slit 45 formed. Otherwise, the third embodiment is the same as the second embodiment and bears the same reference numerals.

By the way, in the present invention, in the structure of the resectoscope, the structure of advancing and retreating the finger hanging part and electrode may be properly formed. Also, the electrode tip can be properly positioned by properly setting the length from the tip of the electrode holding space formed in the slit of the electrode fixing member.

It is apparent that, in the first embodiment shown, for example, in FIG. 1, the pressure part 23 can be fitted to the opposite side surface of the movable member 11.

Further, for example, in FIG. 2, the slit 21 formed in the electrode fixing member 22 can be formed in the horizontal direction (at right angles with the direction shown in FIG. 2), the pressing part 23 can be fitted to the upper side surface of the movable member 11 and the plug connecting part 24 can be fitted to the right or left side surface. In such case, when the part holding the electrode 19 deviates from just above the scope 6, the width of the movable member 11 may be made somewhat larger and the position of providing the space for the electrode fixing member 22 may be displaced.

The present invention includes such modification that, when the shape of the movable member 11 (of a rectangular cross-section) is different, the fitting directions of the pressing part 23 or 55 and plug connecting part 24 or 49 will be different.

Also, in the second embodiment shown, for example, in FIG. 4, in such structure that such slit as in the first embodiment is formed in the small diameter part of the connecting mouthpiece 50, when the movable member 11 and internally provided electrode fixing member 43 are pressed into a communicating hole, the plug connecting part 49 will be able to be well fixed and will be able to be well electrically connected with the electrode fixing member.

As described above, according to the present invention there are advantages that, as the electrode is electrically connected to the electrode cord as uniformly held on the entire periphery by the slit 21 or 45 of the fixing member 22 or 43, the side surface of the rear end part of the electrode 19 and the tip surface of the pressing part 23 or 55 will not be hurt or worn, even in the use for a long period, the electrode will not be hurt or worn in the rear end part, will not fail in the electric contact with the electrode cord and will be able to be well fed with a high frequency current. In the production process, no special step of aligning the pressing member with the current feeding mouthpiece with the electrode held between them is required and the assembling is easy, and. Further, as the part of electrically connecting the electrode 19 in the rear end part with the electrode cord is coated with the insulating member, the device can be operated securely.

By the way, it is apparent that different working modes can be formed in a wide range without deviating from the spirit and scope of the present invention. Therefore, the present invention is not restricted by the specific working mode except being limited in the appended claims.

I claim:

1. A resectoscope comprising:
   (a) a resecting sheath insertable in a body;
   (b) observing scope means positioned in said sheath for observing an affected portion of the body;
   (c) electrode means having a forward end and rear end and positioned in said sheath for resecting the observed affected portion by a high frequency electrical current applied thereto by said forward end;

(d) electrode fixing means comprising an electrically conductive resilient fixing member having a slit therein for receiving the rear end of said electrode means, electrically insulating pressing means for pressing said resilient fixing member into engagement with said electrode means, and electrical plug receiving means with an opening therein, electrically connected to said fixing member, for receiving an electrical plug in the opening therein and electrically connecting the plug to said electrode means through said fixing member; and (e) electrically insulating movable means surrounding said fixing member, said movable means being movable with respect to said sheath such that the movement of said movable means moves said fixing member and said electrode means fixed therein, whereby the forward end of said electrode means extends out of said sheath.

2. A resectoscope according to claim 1, characterized in that said plug receiving means extend from an engaging hole in the electrode fixing member.

3. A resectoscope according to claim 1, characterized in that said plug receiving means is located on the side of said movable means, said receiving means passing through a hole in said movable means and extending into said electrode fixing member.

4. A resectoscope according to claim 1, characterized in that said plug receiving means is formed integrally with the electrode fixing member.

5. A resectoscope according to claim 1, characterized in that said pressing means has an insulating grip and a pressing rod advanced and retreated through an opening in said movable means, said opening facing the pressed surface of the electrode fixing member.

6. A resectoscope according to claim 1, characterized in that said pressing means has a pressing tube adapted to be advanced and retracted and an insulated grip connected to said tube, for advancing and retracting said tube.

* * * * *